(12) United States Patent
Aimiya et al.

(10) Patent No.: US 10,809,167 B2
(45) Date of Patent: Oct. 20, 2020

(54) TISSUE STAINING METHOD WITH STAINING AGENT CONTAINING PARTICLE HOLDING PLURAL PHOSPHORS

(75) Inventors: Takuji Aimiya, Nishitokyo (JP); Hideki Gouda, Tokyo (JP); Hisatake Okada, Tachikawa (JP); Yasushi Nakano, Hino (JP); Kohsuke Gonda, Miyagi (JP); Motohiro Takeda, Miyagi (JP); Noriaki Ohuchi, Miyagi (JP)

(73) Assignee: KONICA MINOLTA, INC., Tokyo (JP)

( * ) Notice: Subject to any disclaimer, the term of this patent is extended or adjusted under 35 U.S.C. 154(b) by 98 days.

(21) Appl. No.: 13/819,574

(22) PCT Filed: Mar. 15, 2011

(86) PCT No.: PCT/JP2011/055991
§ 371 (c)(1),
(2), (4) Date: Feb. 27, 2013

(87) PCT Pub. No.: WO2012/029342
PCT Pub. Date: Mar. 8, 2012

(65) Prior Publication Data
US 2013/0157895 A1    Jun. 20, 2013

(30) Foreign Application Priority Data

Aug. 30, 2010   (JP) ................. 2010-191621
Aug. 31, 2010   (JP) ................. 2010-193153
Aug. 31, 2010   (JP) ................. 2010-193155

(51) Int. Cl.
*G01N 1/30*     (2006.01)
*B82Y 30/00*    (2011.01)
(Continued)

(52) U.S. Cl.
CPC ............... *G01N 1/30* (2013.01); *B82Y 15/00* (2013.01); *B82Y 30/00* (2013.01);
(Continued)

(58) Field of Classification Search
CPC .............. G01N 33/582; G01N 33/588; G01N 21/6428; G01N 33/54313; G01N 1/30;
(Continued)

(56) References Cited

U.S. PATENT DOCUMENTS 4,199,613 A    4/1980    Johnson
4,911,098 A    3/1990    Tabata
(Continued)

FOREIGN PATENT DOCUMENTS

JP          63-66465 A    3/1988
JP       2000-345052 A   12/2000
(Continued)

OTHER PUBLICATIONS

Beverloo et al 1992 Cytometry 13: 561-570.*
(Continued)

*Primary Examiner* — Gailene Gabel
(74) *Attorney, Agent, or Firm* — Lucas & Mercanti, LLP

(57) ABSTRACT

A tissue staining method which comprises: staining a tissue with a staining reagent wherein a biosubstance recognition site is bonded to particles carrying multiple fluorescent substances accumulated therein; in the stained tissue, counting fluorescent points or measuring fluorescent brightness; and evaluating the expression level of a biosubstance, which matches the biosubstance recognition site, in the aforesaid tissue on the basis of the number of the fluorescent points or fluorescent brightness that was measured.

13 Claims, 1 Drawing Sheet

(51) Int. Cl.
 *B82Y 15/00* (2011.01)
 *G01N 33/58* (2006.01)
 *G01N 21/64* (2006.01)
 *G01N 33/74* (2006.01)

(52) U.S. Cl.
 CPC ....... *G01N 21/6428* (2013.01); *G01N 33/582* (2013.01); *G01N 33/588* (2013.01); *G01N 33/74* (2013.01); *G01N 33/743* (2013.01); *G01N 2001/302* (2013.01); *G01N 2021/6441* (2013.01); *G01N 2333/71* (2013.01); *G01N 2333/723* (2013.01); *G01N 2333/91205* (2013.01)

(58) Field of Classification Search
 CPC ..... G01N 2021/6441; G01N 2001/302; G01N 33/74; G01N 2333/71; G01N 2333/723; G01N 2333/91205; B82Y 15/00; B82Y 30/00
 See application file for complete search history.

(56) References Cited

U.S. PATENT DOCUMENTS

| | | | | |
|---|---|---|---|---|
| 5,544,650 | A * | 8/1996 | Boon | G01N 1/30 128/925 |
| 6,492,125 | B2 * | 12/2002 | Kauvar | G01N 33/543 13 435/7.1 |
| 9,625,456 | B2 * | 4/2017 | Bradbury | A61K 51/082 |
| 9,778,273 | B2 * | 10/2017 | Feingold | G01N 1/30 |
| 2003/0015428 | A1 * | 1/2003 | Becker | B03C 5/005 204/547 |
| 2005/0106641 | A1 * | 5/2005 | Kauvar | G01N 15/0625 435/7.21 |
| 2006/0246524 | A1 | 11/2006 | Bauer et al. | |
| 2006/0286626 | A1 * | 12/2006 | Westman | C07D 265/34 435/40.5 |
| 2007/0015226 | A1 * | 1/2007 | Hirai | C07K 16/2863 435/7.23 |
| 2007/0031902 | A1 * | 2/2007 | Pestano | B82Y 30/00 435/7.23 |
| 2009/0109435 | A1 * | 4/2009 | Kahen et al. | 356/317 |
| 2010/0047859 | A1 * | 2/2010 | Lee | B82Y 30/00 435/40.5 |
| 2010/0062451 | A1 * | 3/2010 | Lim | C12P 21/02 435/7.1 |
| 2013/0039848 | A1 * | 2/2013 | Bradbury | A61K 49/0019 424/1.37 |
| 2017/0016911 | A1 * | 1/2017 | Gouda | G01N 33/582 |
| 2018/0045622 | A1 * | 2/2018 | Deisseroth | G01N 1/30 |

FOREIGN PATENT DOCUMENTS

| | | |
|---|---|---|
| JP | 2002-228654 A | 8/2002 |
| JP | 2004-77389 A | 3/2004 |
| JP | 2004-132838 A | 4/2004 |
| JP | 2007-510929 | 4/2004 |
| JP | 2004-286666 A | 10/2004 |
| JP | 2004-300253 A | 10/2004 |
| JP | 2005345764 A | 12/2005 |
| JP | 2006-519376 A | 8/2006 |
| JP | 2007527991 A | 10/2007 |
| JP | 2008-541015 A | 11/2008 |
| JP | 2009-14729 A | 1/2009 |
| WO | 97047968 A1 | 12/1997 |
| WO | WO 99/28856 A1 | 6/1999 |
| WO | 2007074722 A1 | 7/2007 |
| WO | WO 2008/032599 A1 | 3/2008 |
| WO | WO 2008/035569 A1 | 3/2008 |
| WO | WO 2010/016289 A1 | 2/2010 |
| WO | WO 2010/150578 A1 | 12/2010 |

OTHER PUBLICATIONS

"Pathology and Clinical Medicine"; vol. 25, Extra Supplement, Immunohistochemistry useful for diagnosis, Bunkodo, 2007.
Office Action dated Mar. 24, 2015 from the counterpart Japanese Patent Application No. 2014-253705.
English translation Office Action dated Mar. 24, 2015 from the counterpart Japanese Patent Application No. 2014-253705.
Office Action dated Mar. 24, 2015 from the counterpart Japanese Patent Application No. 2014-253709.
English translation of Office Action dated Mar. 24, 2015 from the counterpart Japanese Patent Application No. 2014-253709.
Notification of Reasons for Refusal dated Sep. 20, 2016 from corresponding Japanese Application; Patent Application No. 2015-058870; English translation of Notification of Reasons for Refusal; Total of 10 pages.
Notification of Reasons for Refusal dated Aug. 30, 2016 from corresponding Japanese Application; Patent Application No. 2015-206829; English Translation of Notification of Reasons for Refusal; Total of 7 pages.
Office Action dated Jan. 16, 2018 from the Child U.S. Appl. No. 14/626,329.
Office Action dated Jun. 16, 2017 from corresponding U.S. Appl. No. 14/626,329.
Extended European Search Report dated Aug. 28, 2017 from corresponding European Application No. 17170314.3.
Wang L et al: "Bioconjugated silica nanoparticles: Development and Applications", Nano Research, Tsinghua University Press, CN, vol. 1, No. 2, Jan. 1, 2008 (Jan. 1, 2008), pp. 99-115.
Santra S et al: "Conjugation of Biomolecules With Luminophore-Doped Silica Nanoparticles for Photostable Biomarkers", Analytical Chemistry, American Chemical Society, US, vol. 73, No. 20, Oct. 15, 2001 (Oct. 15, 2001). pp. 4988-4993.
Santra S et al: "Development of novel dye-doped silica nanoparticles for biomarker application", Journal of Biomedical Optics, S Pie-International Society for Optical Engineering, US, vol. 6, No. 2, Apr. 1, 2001 (Apr. 1, 2001), pp. 160-166.
Office Action in the related U.S. Appl. No. 14/626,329, dated Jun. 27, 2019 (18 pages).
Notice of Reasons for Rejection; Patent Application No. 2015-058870; dated Feb. 23, 2016; total of 4 pages. English translation of Notice of Reasons for Rejection; total of 7 pages; Grand Total of 11 pages.

* cited by examiner

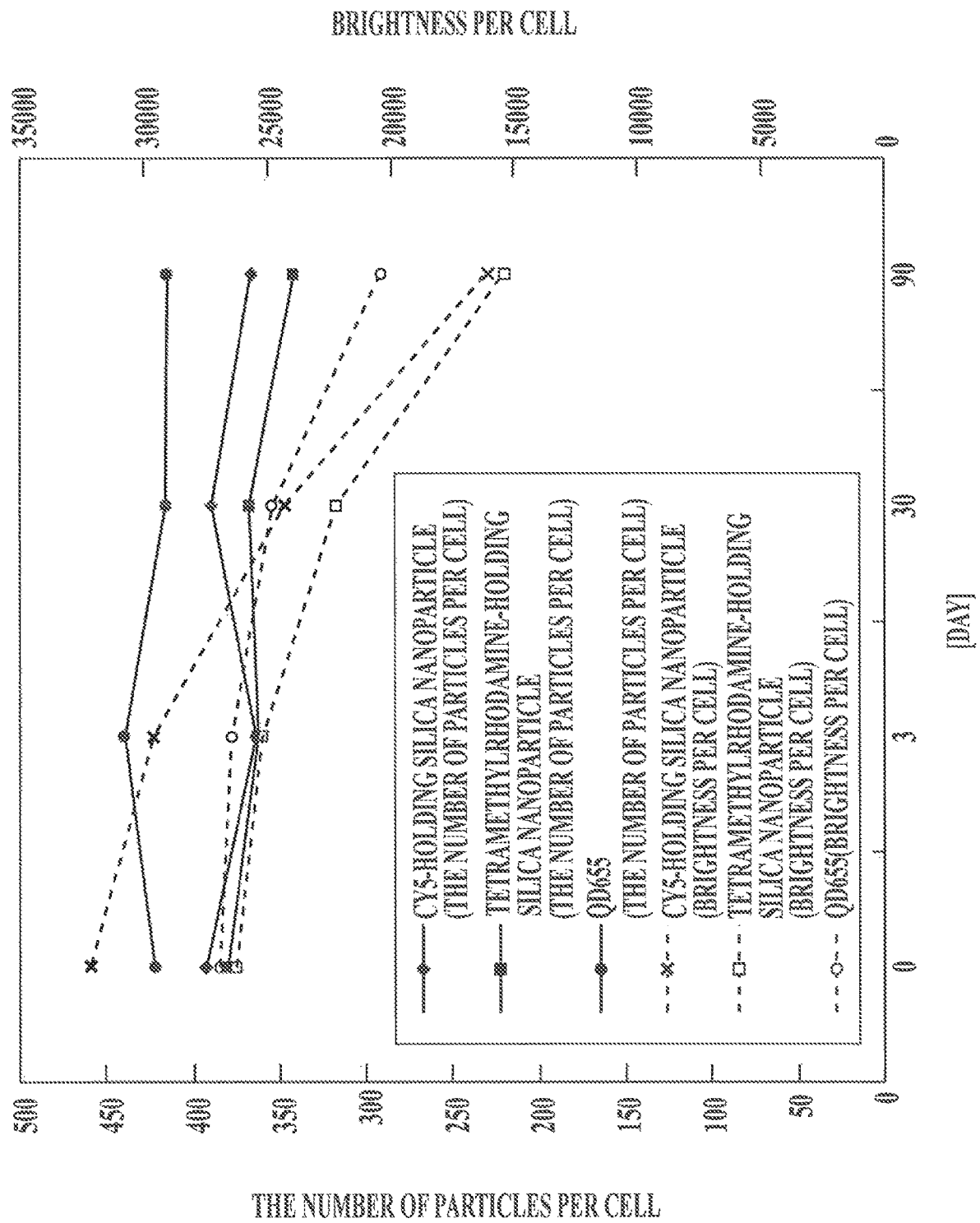

TISSUE STAINING METHOD WITH STAINING AGENT CONTAINING PARTICLE HOLDING PLURAL PHOSPHORS

CROSS REFERENCE TO RELATED APPLICATION

This Application is a 371 of PCT/JP2011/055991 filed on Mar. 15, 2011, which claimed the priority of Japanese Patent Application No. 2010-191621 filed on Aug. 30, 2010; Japanese Patent Application No. 2010-193153 filed on Aug. 31, 2010 and Japanese Patent Application No. 2010-193155 filed Aug. 31, 2010, all applications are incorporated herein by reference in its entirety.

TECHNICAL FIELD

The present invention relates to a tissue staining method, a tissue evaluation method, and a biosubstance detection method.

BACKGROUND ART

In pathological diagnosis, first, a sampled tissue is dehydrated and blocked with paraffin to fix the tissue, then the sample is cut into sections having a thickness of 2 to 8 µm followed by removal of the paraffin therefrom, and subsequently the sections are stained to perform microscopic observation. A pathologist performs diagnosis on the basis of morphological information and staining information such as changes in size and shape of cell nuclei and changes in tissue pattern in the microscopic image. The development of image-digitalizing technology has also facilitated wide use of automated pathological diagnosis support equipment that displays information necessary for pathological diagnosis by a pathologist through extraction and measurement of a pathological image input as a digital color image by using a microscope, a digital camera, or any other device in the field of pathological diagnosis.

For example, Patent Document 1 discloses a pathological diagnosis support equipment including a nucleus/cytoplasm distribution-estimating unit for specifying a cell nucleus region and a cytoplasm region from a pathological image; a glandular cavity distribution-extracting unit for specifying a glandular cavity region (region almost not containing a cellular structure) from a pathological image; a cancer site-estimating unit for determining whether or not cancer cells are present; a stage-determining unit for determining the stage of cancer progression; and an image display unit for displaying, for example, a cancer cell distribution map and the stage of progression.

Patent Document 2 discloses a method to detect cancer cells by staining a pathological specimen with two types of dyes selectively and respectively staining the normal site or the cancer site, evaluating the staining concentrations from a spectral image in accordance with Lambert-Beer's law, and determining whether cancer cells are present.

In each method for evaluation, however, the tissue staining is performed by conventional dye staining (e.g., hematoxylin-eosin staining) or dye staining using an enzyme (e.g., DAB staining), and the staining concentration considerably varies depending on environmental conditions such as temperature and time. Accordingly, such pathological diagnosis support equipments cannot maximize its performance in precise quantitative measurement.

Meanwhile, a fluorescent dye having high sensitivity is also used as a labeling reagent in place of the dye described above in study of tissue staining (see Non-Patent Document 1). The present inventors observed a pathological section prepared with an organic fluorescent dye, FITC, under a fluorescence microscope in accordance with the method of identifying/quantitating cells disclosed in Patent Document 3. Unfortunately, the luminescent brightness was too weak to automatically determine a significantly small amount of biomarker on the basis of the light emission level. Hence, the method requires further improvements.

PRIOR ART DOCUMENTS

Patent Documents

Patent Document 1: Japanese Patent Application Laid-Open Publication No. 2004-286666
Patent Document 2: Japanese Patent Application Laid-Open Publication No. 2001-525580
Patent Document 3: Japanese Patent Application Laid-Open Publication No. Sho 63-66465

Non-Patent Documents

Non-Patent Document 1: "Byori to Rinsyo (Pathology and Clinical Medicine), Vol. 25, 2007, Extra Supplement, Immunohistochemistry useful for diagnosis", Bunkodo, 2007

SUMMARY OF THE INVENTION

Problem to be Solved by the Invention

To such a situation, with the spread of molecular target drug therapy based mainly on antibody drugs, the necessity of exact diagnosis has been increasing recently for more efficient use of the molecular target drugs. It is required to quantitatively detect a significantly small amount of a biomarker on a tissue section so as to perform more exact diagnosis of a disease also in pathological diagnosis. However, in conventional methods of staining pathological tissues, it is difficult to achieve stable quantitation and trace detection capabilities.

The present invention was made in view of the above problems in conventional technologies, and an object of the present invention is to quantitatively detect a small amount of a biosubstance (biomarker).

Means for Solving the Problem

In order to solve the above problems, according to a first aspect of the present invention, there is provided a tissue staining method including
staining a tissue with a staining reagent which includes a particle holding plural phosphors where a biosubstance-recognizing body is bound to the particle.

According to a second aspect of the present invention, there is provided a tissue evaluation method including
staining a tissue section with a staining reagent which contains a phosphor-holding particle holding plural phosphors where a biosubstance-recognizing body is bound to the particle;
counting the number of bright spots of fluorescence in the stained tissue section; and
evaluating an expression level of a biosubstance corresponding to the biosubstance-recognizing body in the stained tissue section on the basis of the number of the counted bright spots.

According to a third aspect of the present invention, there is provided a biosubstance detection method for specifically detecting a biosubstance in a pathological section, and the method includes staining the pathological section with a staining reagent and detecting the biosubstance in the stained pathological section, and in the staining of the pathological section, a first particle holding plural first phosphors where a first biosubstance-recognizing body is bound to the first particle and a second particle holding plural second phosphors having a fluorescence wavelength different from a fluorescence wavelength of the first phosphor where a second biosubstance-recognizing body is bound to the second particle are used as the staining reagent.

Effects of the Invention

According to the first aspect of the present invention, a staining reagent containing a particle holding plural phosphors where a biosubstance-recognizing body is bound to the particle is used. Thus, brightness per particle is high in fluorescence observation, and a small amount of the biosubstance can be quantitatively detected with high sensitivity.

According to the second aspect of the present invention, a small amount of a biosubstance can be quantitatively detected, and further, an expression level of the biosubstance is evaluated on the basis of the number of counted bright spots in a tissue section. As a result, stable evaluation results can be achieved in the quantitative evaluation of the biosubstance.

According to the third aspect of the present invention, a small amount of a biosubstance can be quantitatively detected, and further, particles holding plural phosphors which type has a fluorescence wavelength different from each other where different biosubstance-recognizing bodies are bound to the particles are used. As a result, different biosubstances can be detected by a single pathological section.

BRIEF DESCRIPTION OF THE DRAWINGS

FIG. 1 This is a graph showing changes in the number of particles and brightness per cell with time.

BEST MODE FOR CARRYING OUT THE INVENTION

Hereinafter, embodiments for implementing the present invention will be described. However, the present invention is not limited thereto.

The embodiments provide a tissue staining method, and provide a tissue evaluation method and a biosubstance detection method, each of which uses the tissue staining method.

In the tissue staining method according to the embodiments, phosphor-holding nanoparticles to which biosubstance-recognizing bodies are bound are used.

In the tissue evaluation method according to the embodiments, phosphors or phosphor-holding particles to which biosubstance-recognizing bodies are bound is used, and the number of the phosphors or the phosphor-holding particles which are bound to the biomarker present on the tissue section is determined on the basis of the number of bright spots.

The biosubstance detection method according to the embodiments specifically detects a biosubstance in a pathological section and basically includes a step (1) of staining a pathological section with a staining reagent and a step (2) of detecting the biosubstance in the stained pathological section.

In particular, in the step (2), two types of nanoparticles are used as the staining reagents.

In one type of the nanoparticles, certain biosubstance-recognizing bodies are bound to the nanoparticles, and the nanoparticles hold certain phosphors. In the other type of the nanoparticles, biosubstance-recognizing bodies different from the biosubstance-recognizing bodies of the above type of the nanoparticles are bound to the nanoparticles, and the nanoparticles hold phosphors having a fluorescence wavelength different from a fluorescence wavelength of the phosphor of the above type of the nanoparticles. That is, each type of biosubstance-recognizing bodies different from each of the nanoparticles holds phosphors having fluorescence wavelengths different from each other. Consequently, two different biosubstances corresponding to the biosubstance-recognizing bodies can be detected on the basis of the difference in fluorescence wavelengths of the phosphors. Furthermore, an antigen that has not been identified yet may be specified in the future by selecting biosubstance-recognizing bodies.

In a preferred embodiment of the present invention, use of two types of nanoparticles is exemplified. Alternatively, three or more types of nanoparticles may be used to detect three or more biosubstances as long as their biosubstance-recognizing bodies are different from one another and phosphors (fluorescence wavelengths) are different from each other.

The details of types and characteristics of the phosphors and the like and the biosubstance detection method are as follows.

[Phosphor]

As for the phosphors used in the present invention, organic fluorescent dyes, quantum dots (semiconductor particles), and particles of rare-earth elements can be given as examples. The phosphors preferably emit visual to near-infrared light having a wavelength in the range of 400 to 900 nm when excited with ultraviolet to near-infrared light having a wavelength in the range of 200 to 700 nm.

As for the organic fluorescent dye, fluorescein dye molecules, rhodamine dye molecules, Alexa Fluor (manufactured by Invitrogen Corporation) dye molecules, BODIFY (manufactured by Invitrogen Corporation) dye molecules, cascade dye molecules, coumarin dye molecules, eosin dye molecules, NED dye molecules, pyrene dye molecules, Texas Red dye molecules, cyanine dye molecules, and the like can be given as the example.

Specific examples of the dye can be 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2', 7'-dimethoxyfluorescein, naphthofluorescein, 5-carboxy-rhodamine, 6-carboxy-rhodamine, 5,6-dicarboxy-rhodamine rhodamine 6G, tetramethylrhodamine, X-rhodamine; Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, and BODIPY 650/665 (these are manufactured by Invitrogen Corporation); methoxycoumarin, eosin, NED, pyrene, Cy5, Cy5.5, Cy7, and the like. These dyes may be used alone or in combination of two or more.

As for the quantum dot, either of quantum dots containing a II-VI group compound, a III-V group compound, or a IV group element as a component (also respectively referred to as "II-VI group quantum dot", "III-V group quantum dot", and "IV group quantum dot") can be used. These quantum dots may be used alone or in combination of two or more.

Specific examples of the quantum dots can be, but not limited to, CdSe, CdS, CdTe, ZnSe, ZnS, ZnTe, InP, InN, InAs, InGaP, GaP, GaAs, Si, and Ge.

A quantum dot constituted by the above-mentioned quantum dot as a core and a shell covering the core can also be used. Hereinafter, throughout the description, the quantum dot having a shell is represented by, for example, CdSe/ZnS for a combination of a CdSe core and a ZnS shell. For example, CdSe/ZnS, CdS/ZnS, InF/ZnS, InGaP/ZnS, $Si/SiO_2$, Si/ZnS, $Ge/GeO_2$, or Ge/ZnS can be used, but the quantum dot is not limited thereto.

The quantum dot whose surface is treated with an organic polymer or the like may be used, if necessary. For example, CdSe/ZnS having carboxy groups on the surface (manufactured by Invitrogen Corporation) and CdSe/ZnS having amino groups on the surface (manufactured by Invitrogen Corporation) can be given as examples.

As for the rare-earth element, neodymium oxide, neodymium chloride, neodymium nitrate, ytterbium oxide, ytterbium chloride, ytterbium nitrate, lanthanum oxide, lanthanum chloride, lanthanum nitrate, yttrium oxide, yttrium chloride, yttrium nitrate, praseodymium chloride, erbium chloride, orthophosphoric acid, ammonium phosphate, ammonium dihydrogen phosphate, or the like can be used.

[Particle which Holds Plural Phosphors]

In the present invention, a particle which holds plural phosphors refers to a nanoparticle which disperses phosphors therein (nanoparticle which contains plural phosphors therein (phosphor-containing nanoparticle)), a particle which holds phosphors thereon, or a particle which holds phosphors therein and thereon. The nanoparticle may be chemically bound to the phosphors itself or not.

The nanoparticle may be composed of any material without particular limitation, and such as polystyrene, polylactic acid, and silica can be given as examples.

The particles which holds plural phosphors used in the present invention can be prepared by any known method.

For example, organic fluorescent dye-containing silica nanoparticles can be synthesized with reference to the synthesis of FITC-containing silica particles described in Langmuir, vol. 8, p. 2921, (1992). Various organic fluorescent dye-containing silica particles can be synthesized with a desired organic fluorescent dye instead of FITC.

Quantum dot-containing silica nanoparticles can be synthesized with reference to the synthesis of CdTe-containing silica nanoparticles described in New Journal of Chemistry, vol. 33, p. 561, (2009).

Silica nanoparticles which hold quantum dots thereon can be synthesized with reference to the synthesis of silica nanoparticles containing particles of CdSe/ZnS capped with 5-amino-1-pentanol and APS on the surfaces thereof described in Chemical Communication, p. 2670, (2009).

Organic fluorescent dye-containing polystyrene nanoparticles can be prepared by copolymerization of an organic dye having polymerizable functional groups described in U.S. Pat. No. 4,326,008 (1982) or impregnation of polystyrene nanoparticles with an organic fluorescent dye described in U.S. Pat. No. 5,326,692 (1992).

Quantum dot-containing polymer nanoparticles can be prepared by impregnation of polystyrene nanoparticles with quantum dots described in Nature Biotechnology, vol. 19, p. 631, (2001).

The particles which hold plural phosphors used in the present invention may have any average particle diameter without particular limitation, for example, an average particle diameter of about 30 to 800 nm. If the average particle diameter is less than 30 nm, the amount of phosphors of the particles is insufficient for quantitative evaluation of a target biosubstance. If the average particle diameter exceeds 800 nm, the particles cannot be readily bound to a biosubstance in a pathological tissue. The average particle diameter is preferably in the range of 40 to 500 nm. The reason why the average particle diameter is determined as from 40 to 500 nm is that an average particle diameter less than 40 nm requires an expensive detection system, while an average particle diameter excess 500 nm narrows a range of the quantitative determination due to its physical size. The particles may have any coefficient of variation (=(standard deviation/average value)×100%), which shows a distribution in particle diameter, without particular limitation. Particles having a coefficient of variation of 20% can also be used. The average particle diameter is determined by taking an electron micrograph with a scanning electron microscope (SEM), measuring cross-sectional areas of a sufficient number of particles, and using the diameters of circles each having the same area as the measured cross-sectional area. In the present application, the arithmetic average of particle diameters of 1000 particles is defined as the average particle diameter. The coefficient of variation is calculated also from the particle size distribution of 1000 particles.

[Buffer Solution]

A buffer solution is a solvent for stably maintaining a environment suitable for an antigen-antibody reaction. For example, phosphate buffer physiological saline solutions (PBSs), phosphate buffer solutions, Tris buffer solutions, MES buffer solutions, and citrate-phosphate buffer solutions, and the like can be given as examples.

[Binding of Biosubstance-Recognizing Bodies to Phosphor-Holding Nanoparticles]

The biosubstance-recognizing body according to the present invention is a body which is specifically bound to and/or reacts with a target biosubstance. For example, nucleotide chains, proteins, antibodies, and the like can be given as examples. Specific examples of the body can be an anti-HER2 antibody which is specifically bound to a protein, HER2, present on cell surfaces; an anti-ER antibody which is specifically bound to an estrogen receptor (ER) present on cell nuclei; anti-actin antibody which is specifically bound to actin forming cytoskeletons; and the like. In particular, phosphor-holding nanoparticles to which the anti-HER2 antibodies and the anti-ER antibodies are bound are suitable, because such nanoparticle can be used for selection of a drug for breast cancer.

Biosubstance-recognizing bodies may be bound to a phosphor-holding nanoparticle in any form without particular limitation, and such as covalent bonding, ion bonding, hydrogen bonding, coordinate bonding, physisorption, and chemisorption can be given as examples. In light of the stability of binding, bonding having a strong binding force such as covalent bonding is suitable.

Furthermore, any organic molecule for linking biosubstance-recognizing bodies and a phosphor-holding nanoparticle may be used. For example, in order to inhibit non-specific adsorption to a biosubstance, a polyethylene glycol chain can be used, and SM(PEG)12 manufactured by Thermo Scientific Inc. can be used.

In binding of biosubstance-recognizing bodies to phosphor-holding silica nanoparticles, the same procedure can be used in all cases of using an organic fluorescent dye, quantum dots, or particles of a rare-earth element as the phosphor.

For example, a silane coupling agent, which is a compound widely used for binding an inorganic material with an organic material, can be used. The silane coupling agent is a compound having an alkoxysilyl group which gives a silanol group through hydrosis at one end of the molecule and a functional group at the other end, such as a carboxyl group, an amino group, an epoxy group, or an aldehyde group. The silane coupling agent is bound to an inorganic material via the oxygen atom of the silanol group.

Specifically, mercaptopropyltriethoxysilane, glycidoxypropyltriethoxysilane, aminopropyltriethoxysilane, silane coupling agents having polyethylene glycol chains (e.g., PEG-silane no. SIM6492.7 manufactured by Gelest Inc.), and the like are given as examples of the silane coupling agent. When the silane coupling agents is used, two or more types thereof can be used in combination.

The reaction procedure of the silane coupling agent with organic fluorescent dye-holding silica nanoparticles may be performed by any known method.

For example, prepared organic fluorescent dye-holding silica nanoparticles are dispersed in pure water, and then aminopropyltriethoxysilane is added thereto for a reaction at room temperature for 12 hours. After completion of the reaction, centrifugation or filtration is performed to obtain organic fluorescent dye-holding silica nanoparticles having the surfaces modified with aminopropyl groups. Subsequently, the amino group is made to react with a carboxyl group of an antibody to bind the antibody to the organic fluorescent dye-holding silica nanoparticle via an amide bond. Furthermore, a condensing agent such as 1-ethyl-3-[3-dimethylaminopropyl]carbodiimide hydrochloride (EDC, manufactured by Pierce) may be used as needed.

If necessary, a linker compound having a site that can be directly bound to an organic fluorescent dye-holding silica nanoparticle modified with an organic molecule and a site that can be bound to a target material molecule can be used.

Specifically, by using sulfosuccinimidyl 4-[N-maleimidomethyl]-cyclohexane-1-carboxylate (sulfo-SMCC, manufactured by Pierce) having a site that selectively reacts with an amino group and a site that selectively reacts with a mercapto group, the amino group of an organic fluorescent dye-holding silica nanoparticle modified with aminopropyltriethoxysilane is bound to the mercapto group of an antibody to provide organic fluorescent dye-holding silica nanoparticles to which the antibodies are bound.

Binding of biosubstance-recognizing bodies to a phosphor-holding polystyrene nanoparticle can be achieved by substantially the same procedure in all cases of using an organic fluorescent dye, quantum dots, and particles of a rare-earth element as the phosphor. That is, polystyrene nanoparticles having functional groups such as amino groups are impregnated with an organic fluorescent dye, quantum dots, or particles of a rare-earth element to provide phosphor-holding polystyrene particles having functional groups. A subsequent use of EDC or sulfo-SMCC can provide phosphor-holding polystyrene particles to which the antibodies are bound.

[Staining Method (Biosubstance Detection Method)]

Hereinafter, a staining method (biosubstance detection method) of the present invention will be described.

The staining method of the present invention can be applied to not only pathological tissue sections but also cell staining.

The section to which the staining method of the present invention is applied may be prepared by any known method without particular limitation.

1) Deparaffinization Step

A pathological section is immersed in xylene in a container to remove paraffin. The immersion may be performed at any temperature without particular limitation, for example, at room temperature. The immersion time is preferably 3 minutes or more and 30 minutes or less. The xylene may be replaced with new xylene during the immersion if necessary.

Subsequently, the pathological section is immersed in ethanol in a container to remove xylene. The immersion may be performed at any temperature without particular limitation, for example, at room temperature. The immersion time is preferably 3 minutes or more and 30 minutes or less. The ethanol may be replaced with new ethanol during the immersion if necessary.

Subsequently, the pathological section is immersed in water in a container to remove ethanol. The immersion may be performed at any temperature without particular limitation, for example, at room temperature. The immersion time is preferably 3 minutes or more and 30 minutes or less. The water may be replaced with new water during the immersion if necessary.

2) Activation Treatment

In accordance with a known method, a target biosubstance is subjected to activation treatment.

The activation can be performed under any condition without limitation. As for an activating solution, a 0.01 M citrate buffer solution (pH 6.0), a 1 mM EDTA solution (pH 8.0), 5% urea, a 0.1 M Tris-hydrochloride buffer solution, or the like can be used. As for a heater, an autoclave, a microwave heater, a pressure cooker, a water bath, or the like can be used. The activation may be performed at any temperature without particular limitation, for example, at room temperature. The temperature may range from 50 to 130° C., and the time may range from 5 to 30 minutes.

Subsequently, the section after the activation treatment is washed by being immersed in water and PBS in containers. The washing may be performed at any temperature without particular limitation, for example, at room temperature. Each immersion time is preferably 3 minutes or more and 30 minutes or less. The PBS may be replaced with new PBS during the immersion if necessary.

3) Staining with Phosphor-Holding Nanoparticles to which Biosubstance-Recognizing Bodies are Bound A PBS dispersion of phosphor-holding nanoparticles to which biosubstance-recognizing bodies are bound is placed on a pathological section to react with the target biosubstance. Various biosubstances can be stained by changing the biosubstance-recognizing bodies bound to the phosphor-holding nanoparticles.

In order to simultaneously detect (two or more) different biosubstances, PBS dispersions of the phosphor-holding nanoparticles to which different biosubstance-recognizing bodies are bound are individually prepared, and the dispersions are placed on a pathological section to react with target biosubstances. In the placement on the pathological section, the PBS dispersions of the respective phosphor-holding nanoparticles may be mixed before being placed on a pathological section or may be separately placed on a pathological section. The dispersions may be mixed at any mixing ratio without particular limitation, and the ratio may range from 1:1 to 5:1 for achieving the advantages effect of the present invention.

The PBS dispersion of the phosphor-holding nanoparticles may contain a known blocking agent such as BSA-containing PBS and a surfactant such as Tween 20.

The staining may be performed at any temperature without particular limitation, for example, at room temperature. The reaction time is preferably 30 minutes or more and 24 hours or less.

It is preferred to apply dropwise a known blocking agent such as BSA-containing PBS to the section before the staining with the phosphor-holding nanoparticles.

Subsequently, the stained section is immersed in PBS in a container to remove unreacted phosphor-holding nanoparticles. The PBS solution may contain a surfactant such as Tween 20. The removal may be performed at any temperature without particular limitation, for example, at room temperature. The immersion time is preferably 3 minutes or more and 30 minutes or less. The PBS may be replaced with new PBS during the immersion if necessary.

In order to observe the tissue morphology, hemotoxylin-eosin staining may be performed.

A cover glass is placed on the section for sealing. A commercially available sealing agent may be used as needed.

4) Observation with Fluorescence Microscope

The stained pathological section observed with a fluorescence microscope, and an expression level of the target biosubstance is evaluated on the basis of the number of bright spots or luminescent brightness.

In the count of the number of bright spots or the measurement of luminescent brightness, an excitation light source and a fluorescence detection optical filter are selected so as to correspond to an absorption maximum wavelength and a fluorescence wavelength of used phosphors.

The number of bright spots or luminescent brightness can be counted or measured using an image-analyzing software, e.g., free analysis software ImageJ, or software G-count manufactured by G-Angstrom, for automatically counting all bright spots.

Examples in which the present invention is specifically implemented on the basis of the above-described embodiments will be described, but the present invention should not be limited thereto.

Example 1

Procedure 1: Synthesis of Phosphor-Containing Particles

An organoalkoxysilane compound was obtained by mixing 6.6 mg of tetramethylrhodamine (TAMRA-SE, manufactured by Invitrogen Corporation) and 3 μL of 3-aminopropyltrimethoxysilane (KBM903, manufactured by Shin-Etsu Silicone) in DMF. Then, 0.6 mL of the obtained organoalkoxysilane compound was mixed with 48 mL of ethanol, 0.6 mL of tetraethoxysilane (TEOS), 2 mL of water, and 2 mL of 28% aqueous ammonia for 3 hours.

The liquid mixture prepared in the above step was centrifuged at 10000 G for 20 minutes, and the supernatant was removed. Thereafter, ethanol was added to disperse the precipitate therein, and the dispersion was centrifuged again. The precipitate was washed twice with each of ethanol and pure water by the same procedure.

The obtained tetramethylrhodamine-containing silica nanoparticles were observed with an SEM to measure particle diameters of 200 particles. The average particle diameter was 104 nm, and the coefficient of variation was 12%.

Cy5-containing silica nanoparticles having average particle diameters of 20, 42, 103, 204, and 498 nm were prepared using Cy5-SE (manufactured by Roche) through the same method.

Furthermore, FITC-containing silica nanoparticles having an average particle diameter of 106 nm were prepared using FITC-SE (manufactured by Invitrogen Corporation) through the same method.

Procedure 2: Binding of Antibodies to Phosphor-Containing Particles

Each concentration of the phosphor-containing silica nanoparticles prepared in Procedure 1 (the tetramethylrhodamine-containing silica nanoparticles, the Cy5-containing silica nanoparticles, and the FITC-containing silica nanoparticles) was adjusted to 3 nM with a phosphate buffer physiological saline solution (PBS) containing 2 mM ethylenediaminetetraacetic acid (EDTA). This solution was mixed with a final concentration of 10 mM of SM(PEG)12 (succinimidyl-[(N-maleimidopropionamido)-dodecaethyleneglycol]ester, manufactured by Thermo Scientific Inc. Inc.), followed by reaction for 1 hour. This solution mixture was centrifuged at 10000 G for 20 minutes, and the supernatant was removed. Thereafter, PBS containing 2 mM EDTA is added to disperse the precipitate therein. The dispersion was centrifuged again. The precipitate was washed three times by the same procedure to obtain silica nanoparticles for antibody binding.

Meanwhile, anti-human ER antibodies were subjected to reduction treatment with 1 M dithiothreitol (DTT), and excess DTT the reduced antibodies capable of being bound to the silica nanoparticles.

The silica nanoparticles for antibody binding and the reduced antibody solution obtained above were mixed with each other in PBS containing 2 mM EDTA, followed by reaction for 1 hour. The reaction was stopped by adding 10 mM mercaptoethanol. Then, the obtained solution was centrifuged at 10000 G for 20 minutes, and the supernatant was removed. Thereafter, PBS containing 2 mM EDTA was added to disperse the precipitate therein. The dispersion was centrifuged again. The precipitate was washed three times by the same procedure to obtain phosphor-containing silica nanoparticles to which the anti-human ER antibodies were bound.

Procedure 3: Tissue Staining with Phosphor-Containing Particles

Human mammary tissue was immunostained with the phosphor-containing silica nanoparticles to which the anti-human ER antibodies prepared in Procedure 2 were bound. A tissue array slide (CB-A712) manufactured by Cosmo Bio Co., Ltd. was used as a section to be stained. The tissue array slide was deparaffinized, and washed by being immersed in xylene, ethanol, and water which were substituted in this order, and subsequently subjected to autoclave treatment in a 10 mM citrate buffer solution (pH 6.0) for 15 minutes to perform the activation treatment of the antigen. The tissue array slide after the activation treatment of the antigen was washed with a PBS buffer solution and was subjected to blocking treatment with a PBS buffer solution containing 1% BSA in a moist chamber for 1 hour.

After the blocking treatment, each type of the phosphor-containing silica nanoparticles to which the anti-human ER antibodies were bound was diluted with a PBS buffer solution containing 1% BSA to 0.05 nM and was made to with the tissue section for 3 hours. After the reaction with the phosphor-containing silica nanoparticles to which the anti-human ER antibodies were bound, the tissue array slide was washed with a PBS buffer solution and was sealed with Aquatex manufactured by Merck Chemicals.

Procedure 4: Count of Bright Spots in Tissue Stained with Phosphor-Containing Particles An image of the tissue section stained in Procedure 3 was taken using a DSU confocal microscope manufactured by Olympus Corporation, and bright spots were counted with a bright spot-counting software G-count manufactured by G-Angstrom.

Cy5 was observed with a filter set of an excitation filter (640/30 nm band path filter), a beam splitter (660 nm), and a fluorescence filter (690/50 nm band path filter).

Tetramethylrhodamine was observed with a filter set of an excitation filter (550/25 nm band path filter), a beam splitter (570 nm), and a fluorescence filter (605/70 nm band path filter).

FITC was observed with a filter set of an excitation filter (470/40 nm band path filter), a beam splitter (495 nm), and a fluorescence filter (525/50 nm band path filter).

The number of bright spots in 30 cells was counted for each of eight areas in the tissue array slide which areas were anticipated to show different staining concentrations in preliminary DAB staining to determine the number (mean value) of bright spots per cell. Similarly, luminescent brightness of 30 cells was measured for each of the eight areas to determine luminescent brightness (mean value) per cell.

Comparative Example

Tissue Staining with Fluorescent Dye Alone

As a comparative example, a tissue array slide was stained as in Procedure 3 with anti-human ER antibodies bound to fluorescent dye alone of Cy5, tetramethylrhodamine, or FITC. Bright spots in the tissue were counted as in Procedure 4.

Specifically, eight areas in the tissue array slide were each measured for the number of bright spots and luminescent brightness of 30 cells for each dye to determine the number of bright spots per cell and luminescent brightness per cell.

[Experimental Results A]

A difference in detection sensitivity for the biomarker (ER) due to a difference in fluorescent dye contained in the labeling object (i.e., difference in emission wavelength) was examined.

Table 1 shows the numbers of bright spots per cell counted in the cases of using Cy5-containing silica nanoparticles (average particle diameter: 103 nm), tetramethylrhodamine-containing silica nanoparticles (average particle diameter: 104 nm) and FITC-containing silica nanoparticles (average particle diameter: 106 nm). In Table 1, "−" denotes that no bright spot having a higher brightness than the background level was present, and "+" denotes that the light emission was too strong to be distinguished from bright spots on the periphery.

TABLE 1

LUMINESCENCE WAVELENGTH OF LABELING OBJECT AND THE NUMBER OF BRIGHT SPOTS PER CELL

| LABELING OBJECT | AREA NUMBER | | | | | | | |
|---|---|---|---|---|---|---|---|---|
| | 1 | 2 | 3 | 4 | 5 | 6 | 7 | 8 |
| Cy5-containing silica nanoparticle | − | 4 | 14 | 32 | 120 | 392 | + | + |
| Tetramethylrhodamine-containing silica nanoparticle | − | 6 | 12 | 34 | 112 | 380 | + | + |
| FITC-containing silica nanoparticle | − | − | 10 | 36 | 118 | 381 | + | + |

As shown in Table 1, in all the phosphor-containing particles, the biomarker can be quantitatively evaluated on the basis of the difference of the number of the bright spots. In the tissue section of area No. 2, however, bright spots higher than the background level were not counted in the case of using the FITC-containing nanoparticles, whereas the number of bright spots were counted in the cases of using the Cy5-containing silica nanoparticles and the tetramethylrhodamine-containing silica nanoparticles. Thus, it is revealed that the particles containing a fluorescent dye having a longer excitation wavelength, Cy5 (excitation wavelength: 650 nm, emission wavelength: 670 nm) or tetramethylrhodamine (excitation wavelength: 550 nm, emission wavelength: 570 nm) can detect a smaller amount of biomarker compared with the particles containing FITC (excitation wavelength: 495 nm, emission wavelength: 520 nm).

[Experimental Results B]

A difference in detection sensitivity for the biomarker (ER) due to a difference in particle diameter of the labeling object was examined.

Table 2 shows the numbers of the bright spots per cell counted in the cases of using each types of the Cy5-containing silica nanoparticles (average particle diameter: 20, 42, 103, 204, and 498 nm) and Cy5 dye alone (Comparative Example). In Table 2, "−" denotes that no bright spot having a higher brightness than the background level was present, and "+" denotes that the light emission was too strong to be distinguished from bright spots on the periphery.

TABLE 2

PARTICLE DIAMETER OF LABELING OBJECT AND THE NUMBER OF BRIGHT SPOTS PER CELL

| LABELING OBJECT | AREA NUMBER | | | | | | | |
|---|---|---|---|---|---|---|---|---|
| | 1 | 2 | 3 | 4 | 5 | 6 | 7 | 8 |
| Cy5 dye alone | − | − | − | − | + | + | + | + |
| Cy5-containing silica nanoparticle/average particle diameter: 20 nm | − | − | − | − | + | + | + | + |
| Cy5-containing silica nanoparticle/average particle diameter: 42 nm | − | − | 12 | 39 | 129 | 406 | + | + |
| Cy5-containing silica nanoparticle/average particle diameter: 103 nm | − | 4 | 14 | 32 | 120 | 392 | + | + |
| Cy5-containing silica nanoparticle/average particle diameter: 204 nm | − | 4 | 10 | 36 | 114 | 383 | + | + |
| Cy5-containing silica nanoparticle/average particle diameter: 498 nm | − | 6 | 13 | 33 | 122 | + | + | + |

TABLE 2-continued

PARTICLE DIAMETER OF LABELING OBJECT AND
THE NUMBER OF BRIGHT SPOTS PER CELL

| LABELING OBJECT | AREA NUMBER | | | | | | | |
|---|---|---|---|---|---|---|---|---|
| | 1 | 2 | 3 | 4 | 5 | 6 | 7 | 8 |

−: no bright spot having a higher brightness than the background level was present
+: the light emission was too strong to be distinguished from bright spots on the periphery As shown in Table 2, in the cases of using the Cy5-containing silica nanoparticles having an average particle diameter of 42, 103, 204, or 498 nm, it was possible to quantitatively evaluate the biomarker on the basis of the difference in the number of the bright spots in each area where it was possible to count the number of the bright spots. However, in the case of using the Cy5-containing silica nanoparticles having an average particle diameter of 498 nm, it was not possible to distinguish bright spots from one another in the tissue section of area No. 6. Thus, it is revealed that the quantification range is narrower when a biomarker is expressed with a high frequency.

In addition, in the cases of using the Cy5 dye alone and the Cy5-containing silica nanoparticles having an average particle diameter of 20 nm, no bright spot higher than background level was present in the tissue sections of area Nos. 1 to 4, and bright spots were not distinguished from those on the periphery in the tissue sections of area Nos. 5 to 8. Thus, it is revealed that a small amount of biomarker cannot be quantitatively evaluated by a level of bright spots.

[Experimental Results C]

Detection sensitivities of fluorescent dye-containing particles and fluorescent dye alone for a biomarker (ER) were compared by the number of bright spots.

Table 3 shows the numbers of the bright spots per cell that were counted in each case of using Cy5-containing silica nanoparticles (average particle diameter: 103 nm), tetramethylrhodamine-containing silica nanoparticles (average particle diameter 104 nm), FITC-containing silica nanoparticles (average particle diameter: 106 nm) Cy5, tetramethylrhodamine, or FITC. In Table 3, "−" denotes that no bright spot having a higher brightness than the background level was present, and "+" denotes that the light emission was too strong to be distinguished from bright spots on the periphery.

TABLE 3

COMPARISON OF STAINING BETWEEN DYE-CONTAINING PARTICLE AND DYE ALONE
(THE NUMBER OF BRIGHT SPOTS)

| LABELING OBJECT | AREA NUMBER | | | | | | | |
|---|---|---|---|---|---|---|---|---|
| | 1 | 2 | 3 | 4 | 5 | 6 | 7 | 8 |
| Cy5-containing silica nanoparticle | − | 4 | 14 | 32 | 120 | 392 | + | + |
| Tetramethylrhodamine-containing silica nanoparticle | − | 6 | 12 | 34 | 112 | 380 | + | + |
| FITC-containing silica nanoparticle | − | − | 10 | 36 | 118 | 381 | + | + |
| Cy5 | − | − | − | − | + | + | + | + |
| Tetramethylrhodamine | − | − | − | − | + | + | + | + |
| FITC | − | − | − | − | + | + | + | + |

−: no bright spot having a higher brightness than the background level was present
+: the light emission was too strong to be distinguished from bright spots on the periphery As shown in Table 3, in the ease of tissue staining using fluorescent dye alone, no bright spot in the tissue sections of area Nos. 1 to 4 having a brightness higher than the background level was present, and bright spots in the tissue sections of area Nos. 5 to 8 were not distinguished from those on the periphery. Thus, it is revealed that a small amount of biomarker cannot be quantitatively evaluated by a level of bright spots.

In contrast, in the cases of using phosphor-containing particles as the labeling object, a small amount of biomarker can also be quantitatively determined with high accuracy.

[Experimental Results D]

Detection sensitivities of fluorescent dye-containing particles and fluorescent dye alone for a biomarker (ER) were compared by luminescent brightness.

Table 4 shows the luminescent brightness per cell measured on the basis of image data obtained using a DSU confocal microscope in each case of using Cy5-containing nanoparticles (average particle diameter: 103 nm), tetramethylrhodamine-containing silica nanoparticles (average particle diameter: 104 nm) FITC-containing silica nanoparticles (average particle diameter: 106 nm) Cy5, tetramethylrhodamine, or FITC. The unit of luminescent brightness is a.u. (arbitrary unit). In Table 4, "0" denotes that the light emission was lower than the background level.

TABLE 4

COMPARISON OF STAINING BETWEEN DYE-CONTAINING
PARTICLE AND DYE ALONE (LUMINESCENT BRIGHTNESS)

| LABELING OBJECT | AREA NUMBER | | | | | | | |
|---|---|---|---|---|---|---|---|---|
| | 1 | 2 | 3 | 4 | 5 | 6 | 7 | 8 |
| Cy5-containing silica nanoparticle | 0 | 42 | 160 | 390 | 1280 | 3920 | 9860 | 12333 |
| Tetramethylrhodamine-containing silica nanoparticle | 0 | 60 | 143 | 366 | 1190 | 3686 | 10024 | 11369 |
| FITC-containing silica nanoparticle | 0 | 0 | 112 | 382 | 1220 | 3842 | 10211 | 12488 |
| Cy5 | 0 | 0 | 0 | 0 | 38 | 118 | 260 | 360 |
| Tetramethylrhodamine | 0 | 0 | 0 | 0 | 33 | 129 | 248 | 393 |
| FITC | 0 | 0 | 0 | 0 | 24 | 120 | 263 | 386 |

0: the light emission was lower than the background level

As shown in Table 4, it is revealed that a smaller amount of a biomarker can be detected by using phosphor-containing particles compared to the case of using fluorescent dye alone.

As described above, the use of particles holding plural phosphors where a biosubstance-recognizing bodies are bound to the particles as a staining reagent increases brightness per particle in fluorescence observation of a tissue section, and thereby allows quantitative detection of a small amount of a biomarker (biosubstance corresponding to the biosubstance-recognizing body) with high sensitivity.

In addition, in the use of particles containing plural phosphors, since the phosphors are present inside the particle, the durability of the phosphors is enhanced.

Example 2

[Procedure 1: Synthesis of Phosphor-Containing Particles]

The liquid mixture prepared by the above steps was centrifuged at 10000 G for 20 minutes, and the supernatant was removed. Thereafter, ethanol was added to disperse the precipitate therein, and the liquid mixture was centrifuged again. The precipitate was washed twice with each of ethanol and pure water by the same procedure.

The obtained tetramethylrhodamine-containing silica nanoparticles were observed with an SEM to measure particle diameters of 200 particles. The average particle diameter was 104 nm, and the coefficient of variation was 12%.

Cy5-containing silica nanoparticles having an average particle diameter of 103 nm were obtained using Cy5-SE (manufactured by Roche) (excitation wavelength: 650 nm, emission wavelength: 670 nm) by the same method.

[Procedure 2: Binding of Antibodies to of Phosphor-Containing Particles and Quantum Dot]

Each concentration of the phosphor-containing silica nanoparticles prepared in Procedure 1 (the tetramethylrhodamine-containing silica nanoparticles and the Cy5-containing silica nanoparticles) was adjusted to 3 nM with a phosphate buffer physiological saline solution (PBS) containing 2 mM ethylenediaminetetraacetic acid (EDTA). This solution was mixed with a final concentration of 10 mM of SM(PEG)12 (succinimidyl-RN-maleimidopropionamido)-dodecaethyleneglycol) ester, manufactured by Thermo Scientific Inc. Inc.), followed by reaction for 1 hour. This solution mixture was centrifuged at 10000 G for 20 minutes, and the supernatant was removed. Thereafter. PBS containing 2 mM EDTA was added to disperse the precipitate therein. The dispersion was centrifuged again. The precipitate was washed three times by the same procedure to obtain silica nanoparticles for antibody binding.

Meanwhile, anti-human ER antibodies were subjected to reduction treatment with 1 M dithiothreitol (DTT), and excess DTT was removed by a gel filtration column to obtain a solution of reduced antibodies capable of bonding to silica particles.

The silica nanoparticles for antibody binding and the reduced antibody solution obtained above were mixed with each other in PBS containing 2 mM EDTA, followed by reaction for 1 hour. The reaction was stopped by adding 10 mM mercaptoethanol. Thereafter, the obtained solution was centrifuged at 10000 G for 20 minutes, and the supernatant was removed. Thereafter. PBS containing 2 mM EDTA was added to disperse the precipitate therein. The solution was centrifuged again. The precipitate was washed three times by the same procedure to obtain phosphor-containing silica nanoparticles to which the anti-human ER antibodies were bound.

Anti-human. ER antibodies were bound to quantum dots using a QD655 antibody labeling kit (Q22021MP) manufactured by Invitrogen Corporation. The binding of the antibodies was performed as prescribed in the kit through a step of activating the quantum dots by SMCC and a step of reducing the antibodies by DTT.

[Procedure 3: Tissue Staining with Phosphor Holding Phosphor-Containing Particles or Quantum Dots]

Human mammary tissue was immunostained with the phosphor-holding silica nanoparticles to which the anti-human ER antibodies were bound, and with the quantum dots to which the anti-human ER antibodies prepared in Procedure 2 were bound. A tissue array slide (CB-A712) manufactured by Cosmo Bio Co., Ltd was used as a section to be stained. The tissue array slide was deparaffinized, was then washed by being immersed in xylene, ethanol, and water which were substituted in this order, and was subjected to autoclave treatment in a 10 mM citrate buffer solution (pH 6.0) for 15 minutes to activate the antigen. The tissue array slide after the activation treatment of the antigen was washed with a PBS buffer solution and was subjected to blocking treatment with a PBS buffer solution containing 1% BSA in a moist chamber for 1 hour.

After the blocking treatment, the phosphor-containing silica nanoparticles to which the anti-human ER antibodies were bound and the quantum dots to which the anti-human ER antibodies were bound were each diluted with a PBS buffer solution containing 1% BSA to 0.05 nM and were made to react with the tissue section for 3 hours. Subsequently, the tissue array slide was washed with a PBS buffer solution and was sealed with Aquatex manufactured by Merck Chemicals.

Procedure 4: Count or Measurement of Bright Spots, Brightness, and the Number of Particles in Stained Tissue An image of the tissue section stained in Procedure 3 was taken using a DSU confocal microscope manufactured by Olympus Corporation, and bright spots were counted with a bright spot-counting software G-count manufactured by G-Angstrom.

Cy5 was observed with a filter set of an excitation Filter (640/30 nm band path filter), a beam splitter (660 nm), and a fluorescence filter (690/50 nm band path filter).

Tetramethylrhodamine was observed with a filter set of an excitation filter (550/25 nm band path filter), a beam splitter (570 nm), and a fluorescence filter (605/70 nm band path filter).

QD655 was observed with a filter set of an excitation filter (350/50 nm band path filter), a beam splitter (400 nm) and a fluorescence filter (590 nm long path filter).

For each of eight areas in the tissue array slide which areas were anticipated to show different staining concentrations in preliminary DAB staining, the number of bright spots in 60 cells was counted and brightness of each bright spot was measured.

[Experimental Results A]

First, brightness per particle was determined on the basis of brightness distribution of bright spots (the number of bright spots at each brightness level) obtained in each case of using the phosphor-containing particles or the quantum dots. Specifically, the brightness of the highest frequency in the brightness distribution was determined as the brightness per particle.

The bright spots in each of eight areas (60 cells in each area) were counted in each case of using the Cy5-containing nanoparticles, the tetramethylrhodamine-containing silica nanoparticles, or QD655. As a result, the number of the bright spots having a brightness of 82 was the largest in the measurement using the Cy5-containing silica nanoparticles; the number of the bright spots having a brightness of 69 was the largest in the measurement using the tetramethylrhodamine-containing silica nanoparticles; and the number of the bright spots having a brightness of 64 was the largest in the measurement using QD655.

Table 5 shows the brightness distribution of all bright spots in the eight areas (60 cells×8 areas) in each case of using the Cy5-containing silica nanoparticles, the tetramethylrhodamine-containing silica nanoparticles, or QD655. The unit of brightness is au. (arbitrary unit). Table 5 shows the number of the bright spots in each brightness range of 0 to 30, 31 to 60, 61 to 90, 91 to 120, 121 to 150, 151 to 180, 181 to 210, or 211 to 255.

TABLE 5

DISTRIBUTION OF BRIGHTNESS PER BRIGHT SPOT

| LABELING OBJECT | BRIGHTNESS | | | | | | | |
|---|---|---|---|---|---|---|---|---|
| | 0-30 | 31-60 | 61-90 | 91-120 | 121-150 | 151-180 | 181-210 | 211-255 |
| Cy5-containing silica nanoparticle | 4 | 88 | 814 | 41 | 62 | 210 | 42 | 143 |
| tetramethyl-rhodamine-containing silica nanoparticle | 8 | 49 | 923 | 69 | 242 | 42 | 118 | 63 |
| QD655 | 3 | 20 | 1120 | 36 | 242 | 32 | 96 | 66 |

As shown in Table 5, the Cy5-containing silica nanoparticles had peaks in the brightness ranges of 61 to 90, 151 to 180, and 211 to 255. In the Cy5-containing silica nanoparticles, the number of the bright spots having a brightness of 82 was the largest. It was therefore revealed that the brightness of the bright spots included in the brightness range of 151 to 180 was the sum of two particles, and that the brightness of the bright spots included in the brightness range of 211 to 255 was the sum of three particles. Thus, the brightness of one phosphor-containing particle or one quantum dot can be determined on the basis of brightness distribution.

[Experimental Results B]

Next, the "number of particles per cell" was determined in each area by dividing the "sum of brightness per cell" in each area by the "brightness of one particle" under the assumption that brightness of one Cy5-containing silica nanoparticle was 82, brightness of one tetramethylrhodamine-containing silica nanoparticle was 69, and brightness of one particle of QD655 was 64 on the basis of the results in Experimental results A.

Table 6 shows the numbers of the particles per cell in each area in each case of using the Cy5-containing silica nanoparticles, the tetramethylrhodamine-containing silica nanoparticles, or QD655. In Table 6, "–" denotes that no bright spot having a higher brightness than the background level was present.

TABLE 6

LUMINESCENT WAVELENGTH OF LABELING OBJECT AND THE NUMBER OF PARTICLES PER CELL

| LABELING OBJECT | AREA NUMBER | | | | | | | |
|---|---|---|---|---|---|---|---|---|
| | 1 | 2 | 3 | 4 | 5 | 6 | 7 | 8 |
| Cy5-containing silica nanoparticle | – | 4 | 14 | 32 | 120 | 392 | 688 | 811 |
| tetramethylrhodamine-containing silica nanoparticle | – | 6 | 12 | 34 | 112 | 380 | 648 | 863 |
| QD655 | – | – | – | 22 | 98 | 421 | 699 | 920 |

–: no bright spot having a higher brightness than the background level was present As shown in Table 6, the expression level of a biomarker can be quantitatively evaluated by the difference in the number of the particles per cell in each case of the Cy5-containing silica nanoparticles, the tetramethylrhodamine-containing silica nanoparticles, or QD655. However, in the quantitative evaluation of a further smaller amount of biomarker by a level of bright spots (area Nos. 2 and 3), the Cy5-containing silica nanoparticles and the tetramethylrhodamine-containing silica nanoparticles have higher detection sensitivity than 0.0655.

[Experimental Results C]

Time-dependent changes in bright spots in tissue stained with the phosphor-containing particles or the quantum dots were examined.

The number of bright spots and brightness of each bright spot in 60 cells in the tissue section of area No. 6 in the tissue array slide were counted and measured in accordance with Procedure 4 on the 0, 3rd, 30th, and 90th days after preparation of the tissue section stained in accordance with Procedure 3. Then, the number of the particles per cell was calculated by the same way as in Experimental results B. Brightness per cell was calculated by dividing the sum of brightness of bright spots by the number of the cells.

FIG. 1 shows time-dependent changes in the number of the particles per cell and the brightness per cell calculated as for the tissue section of area No. 6 in each case of using the Cy5-containing silica nanoparticles, tetramethylrhodamine-containing silica nanoparticles, or QD655.

FIG. 1 shows that the brightness per cell gradually decreased with the elapsed time from the preparation of the tissue section, whereas the number of the particles per cell was stable even on the 90th day after the preparation of the tissue section. That is, the brightness of fluorescence emitted by each particle gradually decreased, whereas the number of the particles binding to the biomarker present in a tissue section did not change. Consequently, quantitative evaluation of the expression level of the biomarker on the basis of the difference in the number of particles per cell gives more stable results of evaluation.

[Experimental Results D]

Next, the results in the case of staining with the phosphor-containing particles or the quantum dots were compared with the results in the case of using fluorescent dye alone.

As examples of using fluorescent dye alone, Cy5 to which anti-human ER antibodies were bound and tetramethylrhodamine to which anti-human ER antibodies were bound were used, and a tissue array slide was stained therewith by the same way as Procedure 3. The number of the bright spots and the brightness of each bright spot in 60 cells were determined by the same way as Procedure 4 for eight areas in the tissue array slide. The number of the particles per cell was calculated by the same way All as in Experimental results B.

Table 7 shows the numbers of the particles per cell in each area in each case of using the Cy5-holding silica nanoparticles, the tetramethylrhodamine-containing silica nanoparticles. QD655, Cy5, or tetramethylrhodamine. In Table 7, "−" denotes that the light emission was lower than the background level, and "+" denotes that, although the light emission higher than background level was present, no bright spot was determined.

TABLE 7

COMPARISON OF STAINING BETWEEN DYE-CONTAINING PARTICLE AND DYE ALONE
(THE NUMBER OF PARTICLES PER CELL)

| LABELING OBJECT | AREA NUMBER | | | | | | | |
|---|---|---|---|---|---|---|---|---|
| | 1 | 2 | 3 | 4 | 5 | 6 | 7 | 8 |
| Cy5-containing silica nanoparticle | − | 4 | 14 | 32 | 120 | 392 | 688 | 811 |
| tetramethylrhodamine-containing silican anoparticle | − | 6 | 12 | 34 | 112 | 380 | 648 | 863 |
| QD655 | − | − | − | 22 | 98 | 421 | 699 | 920 |
| Cy5 | − | − | − | − | + | + | + | + |
| Tetramethylrhodamine | − | − | − | − | + | + | + | + |

−: the light emission was lower than the background level
+: the light emission higher than background level was present (determination of bright spots was impossible)

Table 7 shows that the tissue staining with fluorescent dye alone cannot evaluate a biomarker quantitatively by a level of bright spots.

As described above, because an expression level of biosubstance is evaluated on the basis of the number of bright spots of fluorescence counted for a tissue section, stable results in quantitative evaluation of a biosubstance can be obtained.

In addition, by using phosphor-containing particles which hold plural phosphors, brightness per particle in fluorescence observation increases. Thus, quantitative detection of a small amount of a biosubstance with high sensitivity can be performed.

Example 3

Synthesis of Phosphor-Containing Nanoparticles a to f

Synthesis Example 1

Organic Fluorescent Dye-Containing Silica: Synthesis of Cy5-Containing Nanoparticles "Nanoparticle a" was prepared by a method of the following Steps (1) to (4):
Step (1): 1 mg (0.00126 mmol) of an N-hydroxysuccinimide ester derivative of Cy5 (manufactured by GE Healthcare) and 400 μL (1.796 mmol) of tetraethoxysilane were mixed.
Step (2): 40 mL of ethanol and 10 mL of 14% aqueous ammonia were mixed.
Step (3): The solution prepared in Step (1) was added to the solution prepared in Step (2) being stirred at room temperature. The stirring was continued for 12 hours from the starting of the addition.
Step (4): The reaction mixture was centrifuged at 10000 G for 60 minutes, and the supernatant was removed. Thereafter, ethanol was added to disperse the precipitate therein. The dispersion was centrifuged again. The precipitate was washed once with each of ethanol and pure water by the same procedure.

The obtained silica nanoparticle a was observed with a scanning electron microscope (SEM, model S-800, manufactured by Hitachi, Ltd.). The average particle diameter was 110 nm, and the coefficient of variation was 12%.

Synthesis Example 2

Organic Fluorescent Dye-Containing Silica: Synthesis of TAMRA-Containing Silica Nanoparticles "Nanoparticle b" was prepared by a method of the following Steps (1) to (4):
Step (1): 2 mg (0.00126 mmol) of an N-hydroxysuccinimide ester derivative of TAMRA (manufactured by GE Healthcare) and 400 μL (1.796 mmol) of tetraethoxysilane were mixed.
Step (2): 40 mL of ethanol and 10 mL of 14% aqueous ammonia were mixed.
Step (3): The solution prepared in Step (1) was added to the solution prepared in Step (2) being stirred at room temperature. The stirring was continued for 1 hours from the starting of the addition.
Step (4): The reaction mixture was centrifuged at 10000 G for 60 minutes, and the supernatant was removed. Thereafter, ethanol was added to disperse the precipitate therein. The dispersion was centrifuged again. The precipitate was washed once with each of ethanol and pure water by the same procedure.

The obtained silica nanoparticle b was observed with a scanning electron microscope (SEM, model S-800, manufactured by Hitachi, Ltd.). The average particle diameter was 100 nm, and the coefficient of variation of 15%.

Synthesis Example 3

Silica Containing Quantum Dots: Synthesis of Silica Nanoparticles Containing CdSe/ZnS Having an Emission Wavelength of 655 nm "Nanoparticle c" was prepared by a method of the following Steps (1) to (4):
Step (1): 10 μL of a CdSe/ZnS decane dispersion (Qdot655, Invitrogen Corporation) and 40 μL of tetraethoxysilane were mixed.
Step (2): 4 mL of ethanol and 1 mL of 14% aqueous ammonia were mixed.
Step (3): The solution prepared in Step (1) was added to the solution prepared in Step (2) being stirred at room temperature. The stirring was continued for 1.2 hours from the starting of the addition.
Step (4): The reaction mixture was centrifuged at 10000 CI for 60 minutes, and the supernatant was removed. Thereafter, ethanol was added to disperse the precipitate therein. The dispersion was centrifuged again. The precipitate was washed once with each of ethanol and pure water by the same procedure.

The obtained silica nanoparticle c was observed with an SEM. The average particle diameter was 130 nm, and the coefficient of variation was 13%.

Synthesis Example 4

Silica Containing Quantum Dots: Synthesis of Silica Nanoparticles Containing CdSe/ZnS Having an Emission Wavelength of 585 nm "Nanoparticle d" was prepared by a method of the following Steps (1) to (4):

Step (1): 10 µL of a CdSe/ZnS decane dispersion (Qdot585, Invitrogen Corporation) and 40 µL of tetraethoxysilane were mixed.

Step 2): 4 mL of ethanol and 1 mL of 14% aqueous ammonia were mixed.

Step (3): The solution prepared in Step (1) was added to the solution prepared in Step (2) being stirred at room temperature. The stirring was continued for 12 hours from the starting of the addition.

Step (4): The reaction mixture was centrifuged at 10000 G for 60 minutes, and the supernatant was removed. Thereafter, ethanol was added to disperse the precipitate therein. The dispersion was centrifuged again. The precipitate was washed once with each of ethanol and pure water by the same procedure.

The obtained silica nanoparticle d was observed with an SEM. The average particle diameter was 120 nm, and the coefficient of variation was 12%.

Synthesis Example 5

Organic Fluorescence Dye-Containing Polystyrene Nanoparticles: Synthesis of Cy5-Containing Polystyrene Nanoparticles "Nanoparticle e" was prepared by a method of the following steps (1) to (3):

Step (1): 1 mg (0.00126 mmol) of an N-hydroxysuccinimide ester derivative of Cy5 (manufactured by GE Healthcare) was dissolved in 60 µL of dichloromethane and 120 µL of ethanol.

Step (2): The solution prepared in Step (1) was added to 1.5 mL of an aqueous dispersion of polystyrene nanoparticles having surface functional amino groups and a particle diameter of 100 nm (manufactured by Micromod) being vigorously stirred. The stirring was continued for 12 hours from the starting of the addition.

Step (3): The reaction mixture was centrifuged at 10000 G for 60 minutes, and the supernatant was removed. Thereafter, ethanol was added to disperse the precipitate therein. The dispersion was centrifuged again. The precipitate was washed once with each of ethanol and pure water by the same procedure.

The obtained polystyrene nanoparticle e was observed with an SEM. The average particle diameter was 100 nm, and the coefficient of variation was 5%.

Synthesis Example 6

Organic Fluorescence Dye-Containing Polystyrene Nanoparticles: Synthesis of TAMRA-Containing Polystyrene Nanoparticles "Nanoparticle f" was prepared by a method of the following steps (1) to (3):

Step (1): 2 mg (0.00126 mmol) of an N-hydroxysuccinimide ester derivative of TAMRA (manufactured by GE Healthcare) was dissolved in 60 µL of dichloromethane and 120 µL of ethanol.

Step (2): The solution prepared in Step (1) was added to 1.5 mL of an aqueous dispersion of polystyrene nanoparticles having surface functional amino groups and a particle diameter of 100 nm (manufactured by Micromod) being vigorously stirred. The stirring was continued for 12 hours from the starting of the addition.

Step (3): The reaction mixture was centrifuged at 10000 G for 60 minutes, and the supernatant was removed. Thereafter, ethanol was added to disperse the precipitate therein. The dispersion was centrifuged again. The precipitate was washed once with each of ethanol and pure water by the same procedure.

The obtained polystyrene nanoparticle f was observed with an SEM. The average particle diameter was 100 nm, and the coefficient of variation was 6%.

[Binding of Antibodies to Phosphor-Containing Silica Nanoparticle]

Binding of antibodies to the phosphor-containing silica nanoparticles a to d was performed by the following procedure.

Specifically, binding of antibodies to each of the nanoparticles a and c was performed through Steps (1) to (9) and (12) to (14) to form "particles A and C", and binding of antibodies to the nanoparticles b and d was performed through Steps (1) to (7), (10), (11), and (15) to (17) to form "particles B and D".

Step (1): 1 mg of each type of the nanoparticles a to d were dispersed in 5 mL of pure water. 100 µL of aminopropyltriethoxysilane aqueous dispersion was added to each dispersion liquid, followed by stirring at room temperature for 12 hours.

Step (2): The reaction mixture was centrifuged at 10000 G for 60 minutes, and the supernatant was removed.

Step (3): Ethanol was added to disperse the precipitate therein. The dispersion was centrifuged again. The precipitate was washed once with each of ethanol and pure water by the same procedure. The obtained amino group-modified silica nanoparticles a to d were subjected to FT-IR measurement. The absorption due to an amino group was observed, and the modification with the amino group was confirmed.

Step (4): The concentration of each amino group-modified silica nanoparticles a to d prepared in Step (3) was adjusted to 3 nM with a phosphate buffer physiological saline solution (PBS) containing 2 mM ethylenediaminetetraacetic acid (EDTA).

Step (5): SM(PEG)12 (succinimidyl-[(N-maleimidopropionamido)-dodecaethyleneglycol]ester, manufactured by Thermo Scientific Inc.) was mixed with each of the solutions prepared in Step (4) into a final concentration of 10 mM, followed by reaction for 1 hour.

Step (6): Each reaction mixture was centrifuged at 10000 G for 60 minutes, and the supernatant was removed.

Step (7): PBS containing 2 mM EDTA was added to disperse the precipitate therein. Each reaction mixture was centrifuged again. The precipitate was washed three times by the same procedure. Finally, the precipitate was re-dispersed in 500 µL of PBS.

Step (8): 100 µg of anti-human ER antibodies were dissolved in 100 µL of PBS, and 1 M dithiothreitol (DTT) was added thereto, followed by reaction for 30 minutes.

Step (9): Excess DTT was removed from the reaction mixture by a gel filtration column to obtain a reduced anti-human ER antibody solution.

Step (10): 100 µg of anti-HER2 antibodies were dissolved in 100 µL of PBS, and 1 M dithiothreitol (DTT) was added thereto, followed by reaction for 30 minutes.

Step (11): Excess DTT was removed from the reaction mixture by a gel filtration column to obtain a reduced anti-HER2 antibody solution.

Step (12): Particle a or c was used as a starting material. The particle dispersion obtained in Step (7) and the reduced anti-human ER antibody solution obtained in Step (9) were mixed in PBS, followed by reaction for 1 hour.

Step (13): The reaction was stopped by adding 4 µL of 10 mM mercaptoethanol.

Step (14): The reaction mixture was centrifuged at 10000 G for 60 minutes, and the supernatant was removed. Thereafter, PBS containing 2 mM EDTA was added to disperse the precipitate therein. The reaction mixture was centrifuged again. The precipitate was washed three times by the same procedure. Finally, the precipitate was re-dispersed in 500 µL of PBS to obtain phosphor-containing silica nanoparticles A and C to which the anti-human ER antibodies were bound.

Step (15): Particle b or d was used as a starting material. The particle dispersion prepared in Step (7) and the reduced anti-HER2 antibody solution prepared in Step (11) were mixed in PBS, followed by reaction for 1 hour.

Step (16): The reaction was stopped by adding 4 of 10 mM mercaptoethanol.

Step (17): The reaction mixture was centrifuged at 10000 G for 60 minutes, and the supernatant was removed. Thereafter, PBS containing 2 mM EDTA was added to disperse the precipitate therein. The reaction mixture was centrifuged again. The precipitate was washed three times by the same procedure. Finally, the precipitate was re-dispersed in 500 µL of PBS to obtain phosphor-containing silica nanoparticles B and D to which the anti-HER2 antibodies were bound.

[Binding of Antibodies to Phosphor-Containing Polystyrene Nanoparticles]

Bindings of antibodies to the phosphor-containing silica nanoparticles e and f were performed by the following procedures.

Specifically, binding of antibodies to the nanoparticle e was performed through Steps (1), (2), and (5) to (7) to form "particle E", and binding of antibodies to the nanoparticle f was performed through Steps (3), (4), and (8) to (10) to form "particle F".

Step (1): 100 µg of anti-human ER antibodies were dissolved in 100 µL of PBS, and 1 NI dithiothreitol (DTT) was added thereto, followed by reaction for 30 minutes.

Step (2): Excess DTT was removed from the reaction mixture by a gel filtration column to obtain a reduced anti-human ER antibody solution.

Step (3): 100 µg of anti-HER2 antibodies were dissolved in 100 µL of PBS, and 1 its dithiothreitol (DTT) was added thereto, followed by reaction for 30 minutes.

Step (4): Excess DTT was removed from the reaction mixture by a gel filtration column to obtain a reduced anti-HER2 antibody solution.

Step (5): The dispersion of the particle e and the reduced anti-human ER antibody solution prepared in Step (2) were mixed in PBS, followed by reaction for 1 hour.

Step (6): The reaction was stopped by adding 4 µL, of 10 mM mercaptoethanol.

Step (7): The reaction mixture was centrifuged at 10000 G for 60 minutes, and the supernatant was removed. Thereafter, PBS containing 2 mM EDTA was added to disperse the precipitate therein. The reaction mixture was centrifuged again. The precipitate was washed three times by the same procedure. Finally, the precipitate was re-dispersed in 500 of PBS to obtain phosphor-containing polystyrene particles E to which the anti-human ER antibodies were bound.

Step (8): The dispersion of the particle f and the reduced anti-human HER2 antibody solution prepared in Step (4) were mixed in PBS, followed by reaction for 1 hour.

Step (9): The reaction was stopped by adding 4 µL of 10 mercaptoethanol.

Step (10): The reaction mixture was centrifuged at 10000 G for 60 minutes, and the supernatant was removed. Thereafter, PBS containing 2 mM EDTA was added to disperse the precipitate therein. The dispersion was centrifuged again. The precipitate was washed three times by the same procedure. Finally, the precipitate was re-dispersed in 500 µL of PBS to obtain phosphor-containing polystyrene particles F to which the anti-HER2 antibodies were bound.

[Binding of Antibodies to Phosphor]

For comparison, "dye G" was prepared by binding anti-human ER antibodies to Cy5, and "dye H" was prepared by binding anti-HER2 antibodies to TAMPA in accordance with the following procedure.

Specifically, dye G was prepared through Steps (1), (2), (5), (6), and (9) to (11), and dye H was prepared through Steps (3), (4), (7), (8), and (12) to (14).

Step (1): 100 µg of anti-human ER antibodies were dissolved in 100 of PBS, and 1 M dithiothreitol (DTT) was added thereto, followed by reaction for 30 minutes.

Step (2): Excess DTT was removed from the reaction mixture by a gel filtration column to obtain a reduced anti-human ER antibody solution.

Step (3): 100 µg of anti-HER2 antibodies were dissolved in 100 µL of PBS, and 1 M dithiothreitol (DTT) was added thereto, followed by reaction for 30 minutes.

Step (4): Excess DTT was removed from the reaction mixture by a gel filtration column to obtain a reduced anti-HER2 antibody solution.

Step (5): The concentration of 1 mg (0.00126 mmol) of an N-hydroxysuccinimide ester derivative of Cy5 (manufactured by GE Healthcare) was adjusted to 3 nM with a phosphate buffer physiological saline solution (PBS) containing 2 mM ethylenediaminetetraacetic acid (EDTA).

Step (6): SM(PEG)12 (succinimidyl-[(N-maleimidopropionamido)-dodecaethyleneglycol]ester, manufactured by Thermo Scientific Inc. Inc.) was mixed with the solution prepared in Step (5) into a final concentration of 10 mM, followed by reaction for 1 hour.

Step (7): The concentration of 2 mg (0.00126 mmol) of an N-hydroxysuccinimide ester derivative of TAMRA (manufactured by GE Healthcare) was adjusted to 3 nM with a phosphate buffer physiological saline solution (PBS) containing 2 mM ethylenediaminetetraacetic acid (EDTA).

Step (8): SM(PEG)12 (succinimidyl-[(N-maleimidopropionamido)-dodecaethyleneglycol]ester, manufactured by Thermo Scientific Inc. Inc.) was mixed with the solution prepared in Step (7) into a final concentration of 10 mM, followed by reaction for 1 hour.

Step (9): The reaction mixture prepared in Step (6) and the reduced anti-human ER antibody solution prepared in Step (2) were mixed in PBS, followed by reaction for 1 hour.

Step (10): The reaction was stopped by adding 4 µL of 10 mM mercaptoethanol.

Step (11): Excess mercaptoethanol was removed by a gel filtration column to obtain a solution of Cy5 to which the reduced anti-human ER antibodies were bound (dye G).

Step (12): The reaction mixture prepared in Step (8) and the reduced anti-HER2 antibody solution prepared in Step (4) were mixed in PBS, followed by reaction for 1 hour.

Step (13): The reaction was stopped by adding 4 of 10 mM mercaptoethanol.

Step (14): Excess mercaptoethanol was removed by a gel filtration column to obtain a solution of TAMRA to which the reduced anti-HER2 antibodies were bound (dye H).

Table 8 shows the characteristics of particles A to F and dyes G and H prepared by the above-described treatments,

TABLE 8

| Particle | | A | B | C | D |
|---|---|---|---|---|---|
| Phosphor-containing nanoparticle | Nanoparticle | a | b | c | d |
| | Phosphor | Cy5 | TAMRA | Qdot655 | Qdot585 |
| | Composition of material | | Silica | | |
| Biomaterial-recognizing body | | Anti-human ER antibody | Anti-HER2 antibody | Anti-human ER antibody | Anti-HER2 antibody |

| Particle | | E | F | Dye G | Dye H |
|---|---|---|---|---|---|
| Phosphor-containing Nanoparticle | Nanoparticle | e | f | — | |
| | Phosphor | Cy5 | TAMRA | CY5 | TAMRA |
| | Composition of material | Polystylene | | — | |
| Biomaterial-recognizing body | | Anti-human ER antibody | Anti-HER2 antibody | Anti-human ER antibody | Anti-HER2 antibody |

[Evaluation Experiment: (1) Tissue Staining with Particles A to F and dyes G and H]

Human mammary tissue was immunostained with particles A to F and dyes G and H prepared above.

A tissue array slide (CB-A712) manufactured by Cosmo Bio Co., Ltd was used for a section to be stained. The ER and HER2 staining concentrations were observed in advance by DAB staining to prepare three different lots: (1) high expression levels of both of ER and HER2, (2) a high expression level of ER and a low expression level of HER2, and (3) low expression levels of both of ER and HER2, and each lot was stained.

(1): A pathological section was immersed in xylene in a container for 30 minutes. Xylene was replaced with new xylene three times during the immersion.

(2): The pathological section was immersed in ethanol in a container for 30 minutes. Ethanol was replaced with new ethanol three times during the immersion.

(3): The pathological section was immersed in water in a container for 30 minutes. Water was replaced with new water three times during the immersion.

(4): The pathological section was immersed in a 10 mM citrate buffer solution (pH 6.0) for 30 minutes.

(5): The section was subjected to autoclave treatment at 121° C. for 10 minutes.

(6): The section after the autoclave treatment was immersed in PBS in a container for 30 minutes.

(7): PBS containing 1% BSA was placed on the tissue, and the tissue was left to stand for 1 hour.

(8): 10 μL of the phosphor-containing nanoparticles A to which the anti-human ER antibodies were bound diluted to 0.05 nM with PBS containing 1% BSA was mixed with 10 μL of the phosphor-containing nanoparticle B to which the anti-HER2 antibodies were bound diluted to 0.05 nM with PBS containing 1% BSA. The mixture was placed on the tissue, and the tissue was left to stand for 3 hours.

(9): 10 μL of the phosphor-containing nanoparticle C to which the anti-human ER antibodies were bound diluted to 0.05 nM with PBS containing 1% BSA was mixed with 10 μL of the phosphor-containing nanoparticle B to which the anti-HER2 antibodies were bound diluted to 0.05 nM with PBS containing 1% BSA. The mixture was placed on the tissue of a different slide from the slide in step (8), and the tissue was left to stand for 3 hours.

(10): 10 μL of the phosphor-containing nanoparticle E to which the anti-human ER antibodies were bound diluted to 0.05 nM with PBS containing 1% BSA was mixed with 10 μL of the phosphor-containing nanoparticle F to which the anti-HER2 antibodies were bound diluted to 0.05 nM with PBS containing 1% BSA. The mixture was placed on the tissue of a different slide from the slides in steps (8) and (9), and the tissue was left to stand for 3 hours.

(11): 10 μL of the dye G to which the anti-human ER antibodies were bound diluted to 0.05 nM with PBS containing 1% BSA was mixed with 10 μL of the dye H to which the anti-HER2 antibodies were bound diluted to 0.05 nM with PBS containing 1% BSA. The mixture was placed on the tissue of a different slide from the slides in steps (8) to (10), and the tissue was left to stand for 3 hours.

(12): The stained section was immersed in PBS in a container for 30 minutes.

(13): Aquatex manufactured by Merck Chemicals was added dropwise to the section, and a cover glass was placed on the section for sealing.

[Evaluation Experiment: (2) Count of Bright Spots in Tissue Stained with Particles A to F and Dyes G and H]

The stained tissue sections were irradiated with excitation light to emit fluorescence. An image of the tissue section was taken with a DSU confocal microscope manufactured by Olympus Corporation, and the number of the bright spots and luminescent brightness were determined using bright spot-counting software G-count manufactured by G-Angstrom.

Cy5 and Qdot655 were observed at an excitation wavelength of 633 nm and a detection wavelength of 660 nm. TAMRA and Qdot585 were observed at an excitation wavelength of 543 nm and a detection wavelength of 580 nm.

The number of bright spots was an average of the numbers of bright spots in 30 cells which were counted for each of eight areas in a tissue array slide. Luminescent brightness was an average of the sum of fluorescence intensities which were determined in the entire visual field for each of the eight areas.

Tables 9 and 10 show the measurement results of the number of the counted bright spots and measurement of luminescent brightness in "Experimental examples 1 to 7" in combinations of the three lots and the particles A to F and dyes G and H.

TABLE 9

| EXPERIMENTAL EXAMPLE | 1: EXAMPLE | 2: EXAMPLE | 3: EXAMPLE | 4: COMPARATIVE EXAMPLE |
|---|---|---|---|---|
| Lot | 1 | | | |
| | ER expression: HIGH/HER2 expression: HIGH | | | |
| Staining reagent | Particles A and B | Particles C and D | Particles E and F | Dyes G and H |

TABLE 9-continued

| EXPERIMENTAL EXAMPLE | | 1: EXAMPLE | 2: EXAMPLE | 3: EXAMPLE | 4: COMPARATIVE EXAMPLE |
|---|---|---|---|---|---|
| The number of bright spots | 660 nm | 150 | 130 | 155 | Detection immposible |
| | 580 nm | 175 | 190 | 180 | Detection immposible |
| Fluorescent strength | 660 nm | 800 | 750 | 820 | Detection immposible |
| | 580 nm | 870 | 980 | 950 | Detection immposible |

TABLE 10

| EXPERIMENTAL EXAMPLE | | 5: EXAMPLE | 6: EXAMPLE | 7: EXAMPLE |
|---|---|---|---|---|
| Lot | | 1 | 2 | 3 |
| | | ER expression: HIGH/ HER2 expression: HIGH | ER expression: HIGH/ HER2 expression: LOW | ER expression: LOW/ HER2 expression: LOW |
| Staining reagent | | | Particles A and B | |
| The number of bright spots | 660 nm | 150 | 170 | 20 |
| | 580 nm | 175 | 20 | 10 |
| Fluorescent strength | 660 nm | 800 | 850 | 160 |
| | 580 nm | 870 | 150 | 100 |

Table 9 shows that in Experimental example 4 where an organic fluorescent dye alone to which the antibodies were bound, the fluorescence intensity was too weak to be distinguished from background light and did not allow detection of the target biosubstance, whereas in Experimental examples 1 to 3 where phosphor-containing particles were used, the fluorescence intensity was high to allow easy detection of the target biosubstance.

Table 10 shows that in Experimental examples 5 to 7 of sections showing different expression levels of ER2 and HER2, the number of the bright spots and the fluorescence intensity vary depending on the respective expression levels and that expression levels of different biosubstances in a single section can be measured by using particles containing different phosphor and different biosubstance-recognizing bodies as a staining reagent.

INDUSTRIAL APPLICABILITY

The present invention is suitable for quantitative detection of a small amount of a biosubstance.

The invention claimed is:

1. A tissue staining method, comprising:
   staining a tissue with a staining reagent which comprises particles each of which comprises (i) an organic fluorescent dye contained in the particle and (ii) a target-substance-recognizing body bonded to the particle,
   wherein the target-substance-recognizing body binds to a target substance present in the stained tissue to enable counting of the number of the target substance as bright spots of fluorescence in the tissue so as to evaluate the existence of the target substance on the basis of the number of the bright spots,
   wherein an average particle diameter of the particles each of which comprises the organic fluorescent dye contained in the particle and the target-substance recognizing body bonded to the particle is in a range of 40 to 500 nm, and a variation coefficient of particle diameter of the particles each of which further comprises the organic fluorescent dye and the target-substance recognizing body is in a range of 5 to 15%.

2. The tissue staining method according to claim 1, wherein
   the organic fluorescent dye is inside each of the particles.

3. The tissue staining method according to claim 1, further comprising counting the number of the bright spots in the stained tissue.

4. The tissue staining method according to claim 3, further comprising evaluating the existence of the target substance in the stained tissue on the basis of the number of the bright spots.

5. The tissue staining method according to claim 1, further comprising:
   determining a brightness per particle based on a brightness distribution of the bright spots in the stained tissue; and
   determining a total number of the particles each including the organic fluorescent dye per cell in the stained tissue by dividing a total brightness per cell by the brightness per particle.

6. The tissue staining method according to claim 1, wherein the target substance is a protein and the target-substance-recognizing body binds to the protein.

7. The tissue staining method according to claim 6, wherein the target-substance-recognizing body comprises an anti-HER2 antibody or an anti-ER antibody.

8. The tissue staining method according to claim 6, wherein the particles are silica nanoparticles or polylactic acid nanoparticles.

9. The tissue staining method according to claim 1, wherein the particles are silica nanoparticles or polylactic acid nanoparticles.

10. The tissue staining method according to claim 1, wherein the organic fluorescent dye comprises at least one dye selected from a group consisting of fluorescein dye molecules, rhodamine dye molecules, green dye molecules, cascade dye molecules, coumarin dye molecules, eosin dye molecules, NBD dye molecules, pyrene dye molecules, red dye molecules, and cyanine dye molecules.

11. The tissue staining method according to claim 1, wherein the organic fluorescent dye has an excitation wavelength of 550-650 nm and an emission wavelength of 570-670 nm.

12. The tissue staining method according to claim 1, wherein the dye is chemically bonded to the particles inside the particles.

13. The tissue staining method according to claim 1, wherein the average particle diameter is 40 to 204 nm.

* * * * *